United States Patent
Strubel et al.

(10) Patent No.: US 10,546,735 B2
(45) Date of Patent: Jan. 28, 2020

(54) METHOD FOR IDENTIFYING MICROORGANISMS VIA MASS SPECTROMETRY AND SCORE NORMALIZATION

(71) Applicant: bioMerieux, Inc., Durham, NC (US)

(72) Inventors: Grégory Strubel, Manosque (FR); Maud Arsac, Saint Chamond (FR); Denis Desseree, Montluel (FR); Pierre-Jean Cotte-Pattat, Lagnieu (FR); Pierre Mahe, Grenoble (FR)

(73) Assignee: BIOMERIEUX, INC., Durham, NC (US)

( * ) Notice: Subject to any disclaimer, the term of this patent is extended or adjusted under 35 U.S.C. 154(b) by 58 days.

(21) Appl. No.: 14/361,885

(22) PCT Filed: Nov. 30, 2012

(86) PCT No.: PCT/IB2012/056859
§ 371 (c)(1),
(2) Date: May 30, 2014

(87) PCT Pub. No.: WO2013/080169
PCT Pub. Date: Jun. 6, 2013

(65) Prior Publication Data
US 2014/0343864 A1 Nov. 20, 2014

Related U.S. Application Data

(60) Provisional application No. 61/566,029, filed on Dec. 2, 2011.

(30) Foreign Application Priority Data

Dec. 2, 2011 (EP) .................................. 11306609

(51) Int. Cl.
*H01J 49/00* (2006.01)
*G01N 33/483* (2006.01)
*H01J 49/26* (2006.01)

(52) U.S. Cl.
CPC ........ *H01J 49/0036* (2013.01); *G01N 33/483* (2013.01); *H01J 49/26* (2013.01)

(58) Field of Classification Search
None
See application file for complete search history.

(56) References Cited

U.S. PATENT DOCUMENTS

2010/0017356 A1   1/2010   Degrave et al.
2010/0120085 A1   5/2010   Hyman et al.
(Continued)

FOREIGN PATENT DOCUMENTS

CN       101477630 A    7/2009
EP       1253622 A1    10/2002
(Continued)

OTHER PUBLICATIONS

Katrien De Bruyne, Bram Slabbinck, Willem Waegeman, Paul Vauterin, Bernard De Baets, and Peter Vandamme. Bacterial species identification from MALDI-TOF mass spectra through data analysis and machine learning. Feb. 4, 2011, Systematic and Applied Biology, 24, p. 20-29.*

(Continued)

*Primary Examiner* — Olivia M. Wise
(74) *Attorney, Agent, or Firm* — Seckel IP, PLLC (57) ABSTRACT

An identification by mass spectrometry of a microorganism from among reference microorganisms represented by reference data sets includes: determining a set of data of the microorganism according to a spectrum; for each reference microorganism, calculating a distance between the deter- (Continued)

mined and reference sets; and calculating a probability f(m) according to relation $$f(m) = \frac{pN(m \mid \mu, \sigma)}{pN(m \mid \mu, \sigma) + (1-p)N(m \mid \overline{\mu}, \overline{\sigma})}$$

where: m is the distance calculated for the reference microorganism; $N(m\mid\mu,\sigma)$ is the value, for m, of a random variable modeling the distance between a reference microorganism to be identified and the reference microorganism, when the microorganism is the reference microorganism; $N(m\mid\overline{\mu},\overline{\sigma})$ is the value, for m, of a random variable modeling the distance between a microorganism to be identified and the reference microorganism, when the microorganism is not the reference microorganism; and p is a scalar in the range from 0 to 1.

20 Claims, 8 Drawing Sheets

(56) References Cited

U.S. PATENT DOCUMENTS

| 2011/0202282 A1 | 8/2011 | Kostrzewa |
| 2014/0186879 A1 | 7/2014 | Walsh et al. |
| 2014/0288852 A1 | 9/2014 | Ojima et al. |

FOREIGN PATENT DOCUMENTS

| JP | 2007-316063 A | 12/2007 |
| JP | 2012-507711 A | 3/2012 |
| JP | 2013-085517 A | 5/2013 |
| WO | 2010062354 A1 | 6/2010 |

OTHER PUBLICATIONS

Debnath, et al.; "A Decision Based One-Against-One Method for Multi-Class Support Vector Machine"; Jul. 1, 2004; pp. 164-175.
Luts, et al.; "A Tutorial on Support Vector Machine-Based Methods for Classification Problems in Chemometrics"; Apr. 30, 2010; pp. 129-145.
Reddy, et al.; "Chapter 8. Chemometric Methods for Biomedical Raman Spectroscopy and Imaging"; Jan. 1, 2010; pp. 179-213.
Lee, et al.; "Domain Described Support Vector Classifier for Multi-Classification Problems"; Oct. 29, 2006; pp. 41-51.
Schmid, et al.; "Gaussian Mixture Discriminant Analysis for the Single-Cell Differentiation of Bacteria Using Micro-Raman Spectroscopy"; 2009; pp. 159-171.
Rifkin, et al.; "In Defense of One-Vs-All Classification"; 2004; pp. 101-141.
International Search Report Application No. PCT/IB2012/056859 dated Feb. 28, 2013; Mailing Date: Mar. 6, 2013 3 pages.
Fan, et al.; "Liblinear: A Library for Large Linear Classification"; Journal of Machine Learning Research 9 (2008) pp. 1871-1874.
Jackson O. Lay's document, "Maldi-tof spectrometry of bacteria", Mass Spectrometry Reviews, 2001, 20, 172-194. (1 page abstract only).
Lee et al., "Equilibrium-Based Support Vector Machine for Semisupervised Classification", IEEE Transactions on Neural Networks, vol. 18, No. 2, Mar. 2007, pp. 578-583; in English.
Chinese Office Action and Search Report dated Nov. 30, 2016 in corresponding Chinese application No. 201280058681; with English machine translation (22 pages) (D1 De Bruyne et al., Syst. and Appl. Microbial. 2011, 34, 20-29 and D2 Lee et al., Pattern Recognition 2006, 40, 1, 41-51 are not listed in this IDS since they were already listed in the Office Action dated Dec. 30, 2015 and in the IDS filed May 30, 2014, respectively).
Japanese Office Action and Search Report dated May 23, 2016 in corresponding Japanese application No. 2014544030; with English machine translation (43 pages) (D1 De Bruyne et al., Syst. and Appl. Microbiol. 2011, 34, 20-29 and D2 Lee et al., Pattern Recognition 2006, 40, 1, 41-51 are not listed in this IDS since they were already listed in the Office Action dated Dec. 30, 2015 and in the IDS filed May 30, 2014, respectively).

\* cited by examiner

METHOD FOR IDENTIFYING MICROORGANISMS VIA MASS SPECTROMETRY AND SCORE NORMALIZATION

FIELD OF THE INVENTION

The present invention relates to the identification of microorganisms, particularly bacteria, by mass spectrometry.

BACKGROUND OF THE INVENTION

It is known to use mass spectrometry to identify microorganisms, and more particularly bacteria. A sample of the microorganism is prepared, after which a mass spectrum of the sample is acquired and pre-processed, particularly to eliminate the baseline and to eliminate the noise. The peaks of the pre-processed spectrum are then detected and the list of peaks thus obtained is "analyzed" and "compared", by means of classification tools, with data of a knowledge base built from lists of peaks, each associated with an identified microorganism or group of microorganisms (strain, class, family, etc.).

Among classification tools, SVM ("Support Vector Machine") classifications of "one versus all" type are known (hereafter, "OVA SVM"). A "one versus all" SVM classification comprises determining, for each class of objects of a set of classes, an oriented boundary which separates this class from the other classes in the set. As many "one-vs.-all" classifiers as there are classes in the set are thus obtained. The identification of an unknown object then comprises querying each of the classifiers by calculating the algebraic distance between the unknown object and the boundary associated with the classifier. Usually, the unknown object is determined as belonging to the class associated with the largest calculated distance.

Figure 1A:
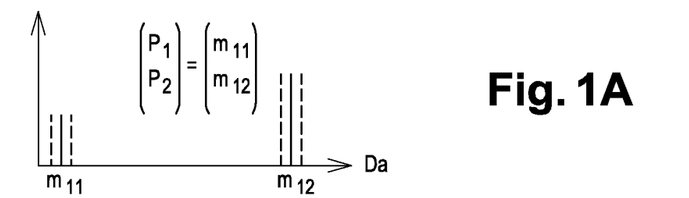
FIGS. 1A, 1B, and 1C are examples of mass spectrums with two peaks characteristic, respectively, of 3 microorganisms.
Figure 1B:
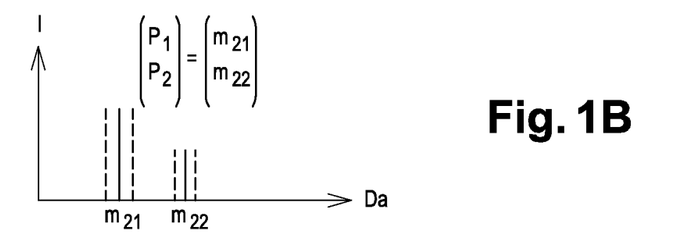
Figure 1C:
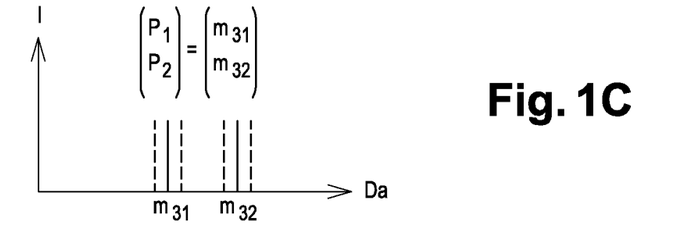
Figure 2:
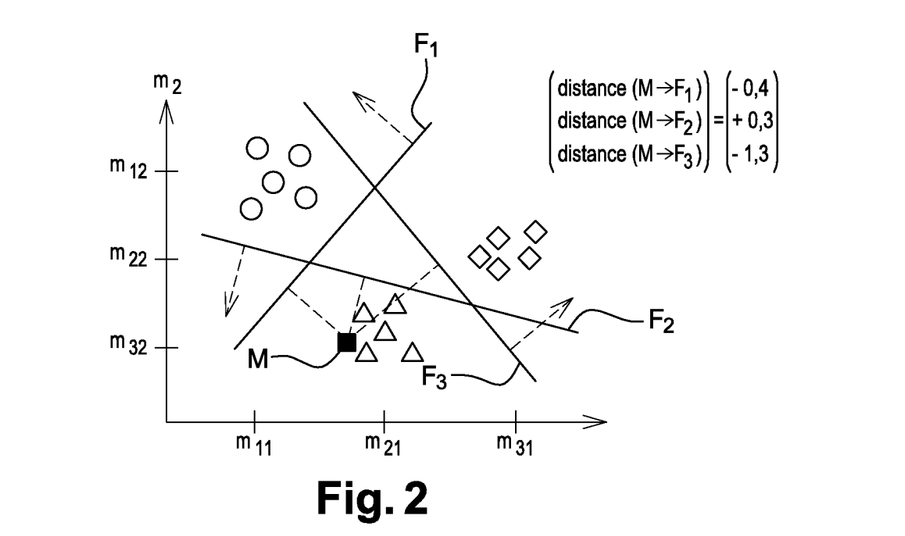
FIG. 2 is a diagram illustrating the obtaining of the three boundaries for the organisms of FIGS. 1A, 1B, 1C by means of a "one-versus-all" SVM algorithm.

This principle is schematically illustrated in FIGS. 1 and 2, which illustrate the very simple case of 3 microorganisms capable of being identified by means of two peaks only in a mass spectrum, for example the two peaks of highest intensity in the mass spectrum of the 3 microorganisms. The first microorganism is characterized by a first peak located on a value m-n and a second peak located on a value $m_{12}$ (FIG. 1A), the second microorganism is characterized by a first peak located on a value $m_{21}$ and a second peak located on a value $m_{22}$ (FIG. 1B), and the third microorganism is characterized by a first peak located on a value $m_{31}$ and a second peak located on a value $m_{32}$ (FIG. 1C).

The OVA SVM classification comprises, first, acquiring a set of training mass spectrums of each of the microorganisms and determining the location of the two concerned peaks in each spectrum, to form a set of training vectors $$\begin{pmatrix} p_1 \\ p_2 \end{pmatrix},$$

$p_1$ being the measured position of the first peak, and $p_2$ being the measured position of the second peak. Due to the measurement uncertainty, a dispersion of the values of the vectors can be observed. In a second step, a boundary separating the set of vectors $$\begin{pmatrix} p_1 \\ p_2 \end{pmatrix}$$

associated with the microorganism from the vectors $$\begin{pmatrix} p_1 \\ p_2 \end{pmatrix}$$

associated with the two other microorganisms is calculated. Three boundaries $F_1$, $F_2$, and $F_3$ are thus obtained, as shown in FIG. 2, and are provided with a direction, for example, that indicated by the arrows in dotted lines.

The identification of an unknown microorganism then comprises acquiring one or a plurality of microorganism mass spectrums, deducing therefrom a vector M of measured peaks $$\begin{pmatrix} p_1 \\ p_2 \end{pmatrix},$$

and calculating the algebraic distance, also called "margin", of this vector M to each of oriented boundaries $F_1$, $F_2$, and $F_3$. An algebraic distance vector, for example, equal to $$\begin{pmatrix} -0.4 \\ +0.3 \\ -1.3 \end{pmatrix},$$

is thus obtained. In the very simple illustrated case, it could thus be deduced that the unknown microorganism is the second microorganism.

Of course, the case illustrated herein is extremely simple. In reality, a microorganism has to be identified from among hundreds of microorganisms with a number of peaks retained for the identification capable of exceeding substantially 1,000 peaks. Further, the illustrated case is also simple since the microorganisms are very distant from one another and the measurement has been performed with enough accuracy to be able to deduce significant information from the distances.

In real cases, it is difficult or even impossible to directly deduce relevant information regarding the calculated distances to the boundaries. Indeed, a distance value may correspond to very different situations. FIGS. 3A to 3D illustrate this principle in a simple fashion. These drawings show boundary $F_1$ separating a set of training peak vectors $$\begin{pmatrix} m_1 \\ m_2 \end{pmatrix}$$

associated with a first microorganism, represented by circles, from the other training peak vectors $$\begin{pmatrix} m_1 \\ m_2 \end{pmatrix}$$

associated with the other microorganisms, represented by triangles. Vectors of measured peaks M of an unknown microorganism to be identified are represented by squares.

Figure 3A:
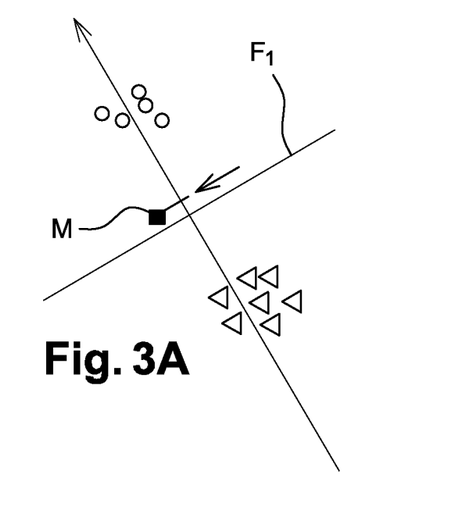
FIGS. 3A to 3D are diagrams illustrating four distance distances from a tested individual to an SVM-type boundary.
Figure 3B:
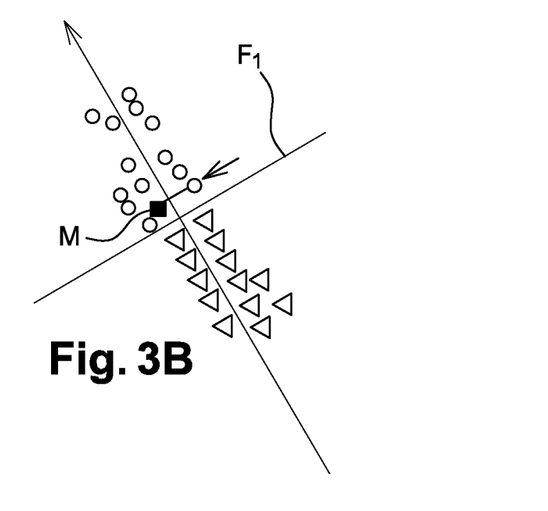
Figure 3C:
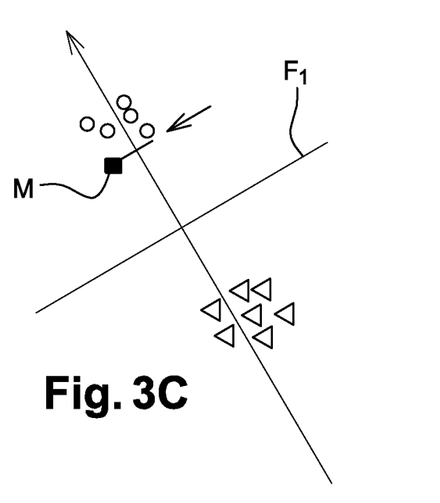
Figure 3D:
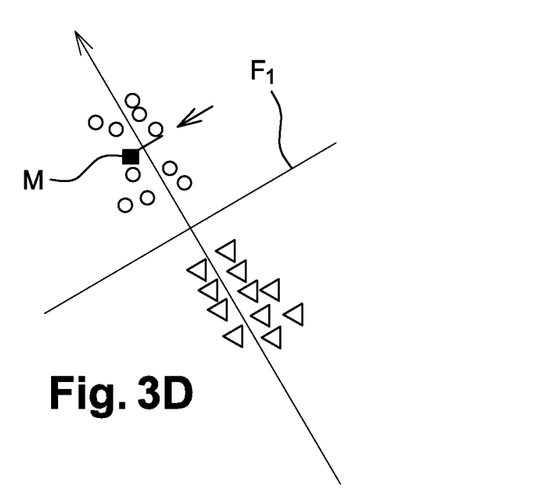

In the case illustrated in FIG. 3A, the distance of measured vector M to boundary $F_1$ is positive. However, vector M is so remote from the set of training vectors of the first microorganism that it cannot be deduced with certainty that the unknown microorganism effectively is the first microorganism. In the case illustrated in FIG. 3B, the measured vector M is now close to the set of training vectors but also very close to the other sets of training vectors. In this case also, it is difficult to deduce that the unknown microorganism is the first microorganism. In the case illustrated in FIG. 3C, measured vector M is distant from boundary $F_1$ and is close to the set of training vectors, while being at the border of this set. Although this case is more favorable than previous cases, there still is an uncertainty as to the where the microorganism to be identified belongs. It is in particular necessary to study the accuracy of the measurement. Finally, the case illustrated in FIG. 3D is the rare typical case where the measured vector is both distant from the boundary and is located among the set of training vectors. The measured distance then is a value characteristic of the first microorganism, and can be relied upon.

As can be observed, the calculated distances are only partially relevant. For example, in a first case, a distance equal to 0.4 is highly relevant while in another case, it is impossible to deduce anything therefrom. It is thus necessary to analyze these distances to deduce the type of unknown microorganism therefrom, as well as the degree of reliance to be had on this identification. This additional analysis step is conventional carried out by an operator, be it a biologist or a doctor, who determines by means of his/her know-how what conclusion can be drawn from the distances calculated by the classification tool.

An SVM-type vector classification has been described, which calculates an algebraic distance between two objects of a vectorial space, that is, a vector corresponding to the microorganism to be identified, and a hyperplane corresponding to a boundary partitioning the space, in the illustrated example, $\mathfrak{R}^2$, into two sub-spaces. The type of problem discussed in relation with this type of classification also appears in other classification types as soon as they generate a value or score representing a distance to reference objects, be the classifications of SVM type or not, or more generally of vector type or not, such as for example Bayesian classifications, linear classifications, classifications based on neural networks, tolerant distance classifications, etc.

To a certain extent, it may be argued that there still exists no reliable tool for identifying microorganisms by means of a mass spectrometry and of classification tools calculating distance values.

SUMMARY OF THE INVENTION

The present invention aims at solving the above-mentioned problem by providing an algorithm for identifying a microorganism based on mass spectrum measurements and classification tools, which enable to more reliably identify a microorganism as compared to previous identification techniques.

For this purpose, an object of the invention is method of identifying by mass spectrometry a microorganism from among a predetermined group of reference microorganisms, each reference microorganism being represented by a set of reference data, the method comprising:

determining a set of data representative of the microorganism to be identified according to a mass spectrometry measurement of said microorganism; and for each reference microorganism, calculating a distance between said determined set of data and the set of reference data of the reference microorganism.

According to the invention, the method comprises calculating a probability for the microorganism to be identified to be the reference microorganism, according to relation:

$$f(m) = \frac{pN(m \mid \mu, \sigma)}{pN(m \mid \mu, \sigma) + (1-p)N(m \mid \bar{\mu}, \bar{\sigma})}$$

where:

m is the distance calculated for the reference microorganism;

f(m) is the probability calculated for said distance m;

$N(m|\mu,\sigma)$ is the value, for distance m, of a random variable modeling the distance between a set of data associated with a microorganism to be identified and the set of reference data of the reference microorganism, when the microorganism to be identified is the reference microorganism;

$N(m|\bar{\mu},\bar{\sigma})$ is the value, for distance m, of a random variable modeling the distance between a set of data associated with a microorganism to be identified and the set of reference data of the reference microorganism, when the microorganism to be identified is not the reference microorganism; and p is a predetermined scalar in the range from 0 to 1.

"Set of reference data" means the data which characterize a reference microorganism in the sense of a classification tool. For example, for an OVA SVM classification, the reference data associated with a reference microorganism correspond to a hyperplane of a vectorial space which partitions this space into two sub-spaces.

"Set of representative data" means the data used to characterize a microorganism to be identified in the sense of the selected classification tool. For example, by the OVA SVM classification, these data are a list of detected peaks which forms a vector in the vectorial space.

In other words, the invention applies to any type of classification. As known per se, a classification generates distances, which are objective quantities measuring distances to reference elements. According to the invention, these distances are transformed into probabilities normalized between 0 and 1 according to a "sigmoid"-type law. As a result, these probabilities are themselves objective quantities comparable with one another, and thus real measurements of the "similarity" of an unknown microorganism with a previously-identified microorganism.

According to an embodiment, random variables $N(m|\mu,\sigma)$ and $N(m|\bar{\mu},\bar{\sigma})$ are Gaussian random variables, having averages respectively equal to $\mu$ and $\bar{\mu}$, and standard deviations respectively equal to $\sigma$ and $\bar{\sigma}$. More particularly, the probability is calculated according to relation:

$$f(m) = \frac{1}{1 + \frac{1-p}{p}\exp\left(\ln\left(\frac{\sigma}{\bar{\sigma}}\right) - \frac{1}{2(\sigma\bar{\sigma})^2}\begin{bmatrix}[(\sigma - \bar{\sigma})m - (\bar{\mu}\sigma - \mu\bar{\sigma})]\\ [(\sigma + \bar{\sigma})m - (\bar{\mu}\sigma + \mu\bar{\sigma})]\end{bmatrix}\right)}$$

Advantageously, if logic relation "$\mu > \bar{\mu}$"$\oplus$"$\sigma > \bar{\sigma}$" is verified, where $\oplus$ represents the "exclusive-or", the probability is set to 1 for any distance m greater than $$\frac{\overline{\mu}\sigma^2 - \mu\overline{\sigma}^2}{\sigma^2 - \overline{\sigma}^2}.$$

Advantageously, if logic relation "$\mu > \overline{\mu}$"$\oplus$"$\sigma > \overline{\sigma}$" is not verified, where $\oplus$ represents the "exclusive-or" function, the probability is set to 0 for any distance m smaller than $$\frac{\overline{\mu}\sigma^2 - \mu\overline{\sigma}^2}{\sigma^2 - \overline{\sigma}^2}.$$

According to an embodiment, scalar p is identical for all reference microorganisms. More particularly, p is equal to $$\frac{1}{N},$$

where N is the size of the set of reference microorganisms. As a variation, scalar p is equal to 0.5.

According to an embodiment of the invention, the determination of the mass spectrum and the calculation of the distance between the acquired spectrum and each reference microorganism implement a vectorial classification algorithm.

More specifically, the determination of the mass spectrum of the microorganism comprises:

a. acquiring at least one mass spectrum of said microorganism;

b. detecting peaks in the at least one acquired mass spectrum and converting the detected peaks into a vector of a predetermined vectorial space, and the calculation of the distance between said microorganism and each reference microorganism comprises calculating an algebraic distance between the determined vector and a boundary which partitions the vectorial space between a first sub-space characteristic of the reference microorganism and a second sub-space characteristic of the other reference microorganisms.

Particularly, the boundary of a reference microorganism is calculated by means of an algorithm of "support vector machine" type and of a set of vectors corresponding to the reference microorganisms.

As a variation, the determination of the mass spectrum and the calculation of the distance between the acquired spectrum and each reference microorganism implement a tolerant distance algorithm.

According to an embodiment, the vector is calculated by identifying at most one peak in each interval of a predetermined subdivision in the range of mass-to-charge ratios of the mass spectrum.

BRIEF DESCRIPTION OF THE DRAWINGS

The present invention will be better understood on reading of the following description provided as an example only in relation with the accompanying drawings, where the same reference numerals designate the same or similar elements, among which.

DETAILED DESCRIPTION OF THE INVENTION

Figure 4:
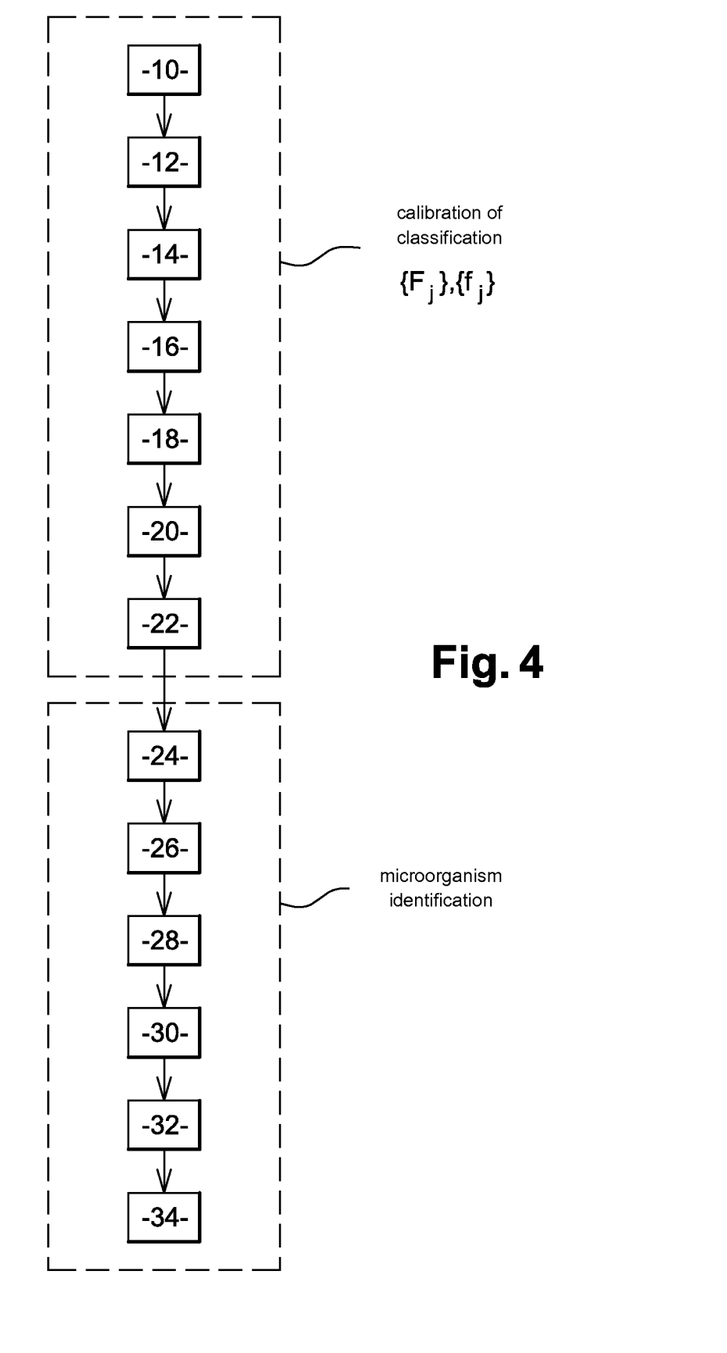
FIG. 4 is a flowchart of a method according to the invention.

A method according to the invention based on OVA SVM classification will now be described in relation with the flowchart of FIG. 4.

The method starts with a step 10 of acquiring a set of training mass spectrums and a set of calibration mass spectrums of a new identified microorganism to be integrated in a knowledge base, for example, by means of a MALDI-TOF ("Matrix-assisted laser desorption/ionization time of flight") mass spectrometry. MALDI-TOF mass spectrometry is well known per se and will not be described in further detail hereafter. Reference may for example be made to Jackson O. Lay's document, "*Maldi-tof spectrometry of bacteria*", Mass Spectrometry Reviews, 2001, 20, 172-194. The acquired spectrums are then preprocessed, particularly to denoise them and remove their baseline, as known per se.

An identification of the peaks present in the acquired spectrums is then performed at step 12, for example, by means of a peak detection algorithm based on the detection of local maximum values. A list of peaks for each acquired spectrum, comprising the location and the intensity of the spectrum peaks, is thus generated.

Advantageously, the peaks are identified in the predetermined Thomson range of $[m_{min}; m_{max}]$, preferably Thomson range $[m_{min}; m_{max}] = [3,000; 17,000]$. Indeed, it has been observed that the information sufficient to identify the microorganisms is contained in this range of mass-to-charge ratios, and that it is thus not needed to take a wider range into account.

The method carries on, at step 14, by a quantization or "binning" step. To achieve this, range $[m_{min}; m_{max}]$ is divided into intervals for example having a constant width and for each interval comprising several peaks, a single peak is kept, advantageously the peak having the highest intensity. A vector is thus generated for each measured spectrum. Each component of the vector corresponds to a quantization interval and has as a value the intensity of the peak kept for this interval, value "0" meaning that no peak has been detected in the interval.

As a variation, the vectors are "binarized" by setting the value of a component of the vector to "1" when a peak is present in the corresponding interval, and to "0" when no peak is present in this interval. This results in making the subsequently performed classification algorithm calibration more robust. The inventors have indeed noted that the information relevant, particularly to identify a bacterium, is essentially contained in the absence and/or the presence of peaks, and that the intensity information is less relevant. It can further be observed that the intensity is highly variable from one spectrum to the other and/or from one spectrometer to the other. Due to this variability, it is difficult to take into account raw intensity values in the classification tools.

In parallel, the training spectrum peak vectors, called "training vectors" hereafter, and the calibration spectrum peak vectors, called "calibration vectors" hereafter, are stored in the knowledge base. For each of the microorganisms recorded in the knowledge base, there thus are a first set $\{V_{i,j}^a\}$ of training vectors $V_{i,j}^a$, and a second set $\{V_{i,j}^c\}$ of calibration vectors $V_{i,j}^c$.

At a next step 16, a boundary $F_j$ is calculated for each microorganism j of the knowledge base between the set of training vectors $\{V_{i,j}^a\}$ of the microorganism and set $\{V_{i,k\neq j}^a\}$ of training vectors $V_{i,k\neq j}^a$ of the other microorganisms. Boundary $F_j$ is calculated by means of an OVA SVM classification algorithm. This algorithm is conventional and for further details, reference may for example be made to R.-E. Fan, K.-W. Chang, C.-J. Hsieh, X.-R. Wang, and C.-J. Lin.'s document "*LIBLINEAR: A Library for Large Linear Classification*", Journal of Machine Learning Research 9(2008), 1871-1874. Software coding this algorithm is for example accessible at address www.csie.ntu.edu.tw/~cjlin/liblinear.

The method then comprises determining a function $f_j$ which transforms the algebraic distance to a boundary $F_j$ into a degree of similarity with microorganism j associated with this boundary $F_j$. The principle underlying this transformation is to consider the distance of a microorganism j to its associated boundary $F_j$ as being a first random variable $N_j(m|\mu_j,\sigma_j)$, and the distance of the other microorganisms to this boundary as being a second random variable $N_j(m|\overline{\mu}_j,\overline{\sigma}_j)$, and then to determine a monotonous function $f_j$, varying from 0 to 1, which separates the two random variables $N_j(m|\mu_j,\sigma_j)$ and $N_j(m|\overline{\mu}_j,\overline{\sigma}_j)$.

The method thus carries on with the identification, at step 18, of these two random variables $N_j(m|\mu_j,\sigma_j)$ and $N_j(m|\overline{\mu}_j,\overline{\sigma}_j)$ for each microorganism j of the knowledge base, based on calibration vectors $\{V_{i,j}^c\}$ and $\{V_{i,k\neq j}^c\}$. Using calibration vectors different from the training vectors used to calculate boundaries $F_j$ avoids an overtraining phenomenon which may adversely affect the robustness and the accuracy of the identification. Of course, it is also possible to use training vectors to calculate functions $f_j$.

Figure 5:
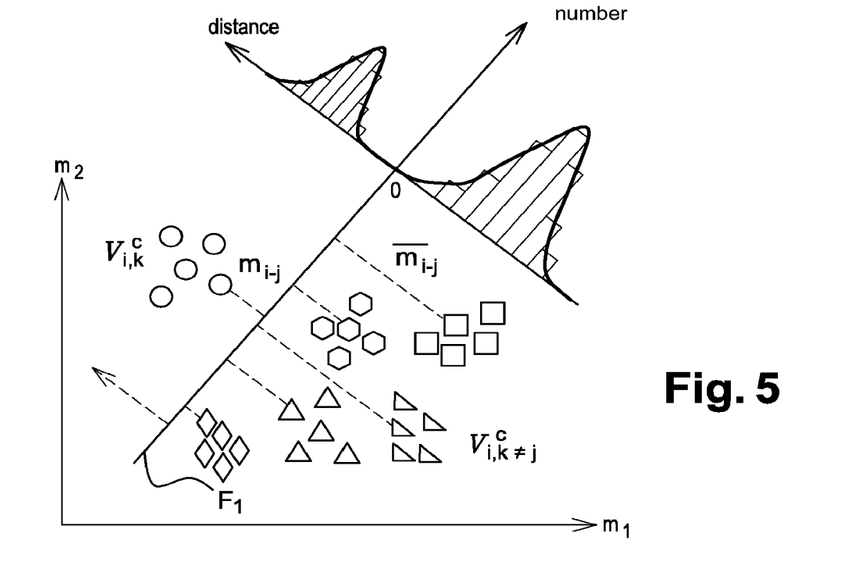
FIG. 5 is a diagram illustrating the determination of two random variables from distances of microorganisms to an SVM-type boundary.

Taking the example of FIGS. 1 and 2 where microorganisms can be identified by the location of two peaks of the mass spectrum, the calculation of these random variables is illustrated in FIG. 5, which shows calibration vectors $V_{i,j}^c$ of a microorganism j, separated by a boundary $F_j$ from calibration vectors $V_{i,k\neq j}^c$ of the other microorganisms of the knowledge base.

First, distance $m_{i,j}$ between each calibration vector $V_{i,j}^c$ of microorganism j and boundary $F_j$ is calculated, as well as distance $\overline{m}_{i,j}$ between each calibration vector $V_{i,k\neq j}^c$ of the other microorganisms of the knowledge base and said boundary $F_j$.

Then, random variable $N_j(m|\mu_j,\sigma_j)$ modeling the distance between a microorganism j and its boundary $F_j$ is identified based on the set of distances $m_{i,j}$, and random variable $N_j(m|\overline{\mu}_j,\overline{\sigma}_j)$ modeling the distance between the other microorganisms and boundary $F_j$ is identified based on the set of distances $\overline{m}_{i,j}$.

Advantageously, the selected random variable model is a Gaussian distribution. Random variables $N_j(m|\mu_j,\sigma_j)$ and $N_j(m|\overline{\mu}_j,\overline{\sigma}_j)$ can thus be written according to relations:

$$N_j(m|\mu_j,\sigma_j) = \frac{1}{\sigma_j\sqrt{2\pi}} \cdot \exp\left(-\frac{1}{2}\left(\frac{m-\mu_j}{\sigma_j}\right)^2\right) \quad (1)$$

$$N_j(m|\overline{\mu}_j,\overline{\sigma}_j) = \frac{1}{\overline{\sigma}_j\sqrt{2\pi}} \cdot \exp\left(-\frac{1}{2}\left(\frac{m-\overline{\mu}_j}{\overline{\sigma}_j}\right)^2\right) \quad (2)$$

$$\mu_j = \frac{1}{M_j^c} \sum_{i=1}^{M_j^c} m_{i,j} \quad (3)$$

$$\sigma_j = \sqrt{\frac{1}{M_j^c - 1} \sum_{i=1}^{M_j^c} (m_{i,j} - \mu_j)^2} \quad (4)$$

$$\overline{\mu}_j = \frac{1}{M_j^{cneg}} \sum_{i=1}^{M_j^{cneg}} \overline{m}_{i,j} \quad (5)$$

$$\overline{\sigma}_j = \sqrt{\frac{1}{M_j^{cneg} - 1} \sum_{i=1}^{M_j^{cneg}} (\overline{m}_{i,j} - \overline{\mu}_j)^2} \quad (6)$$

where m is the distance to boundary $F_j$, $M_j^c$ is the number of calibration vectors $V_{i,j}^c$ of microorganism j, and $M_j^{cneg}$ is the total number of calibration vectors $V_{i,k\neq j}^c$ of the other microorganisms of the knowledge base.

Figure 6:
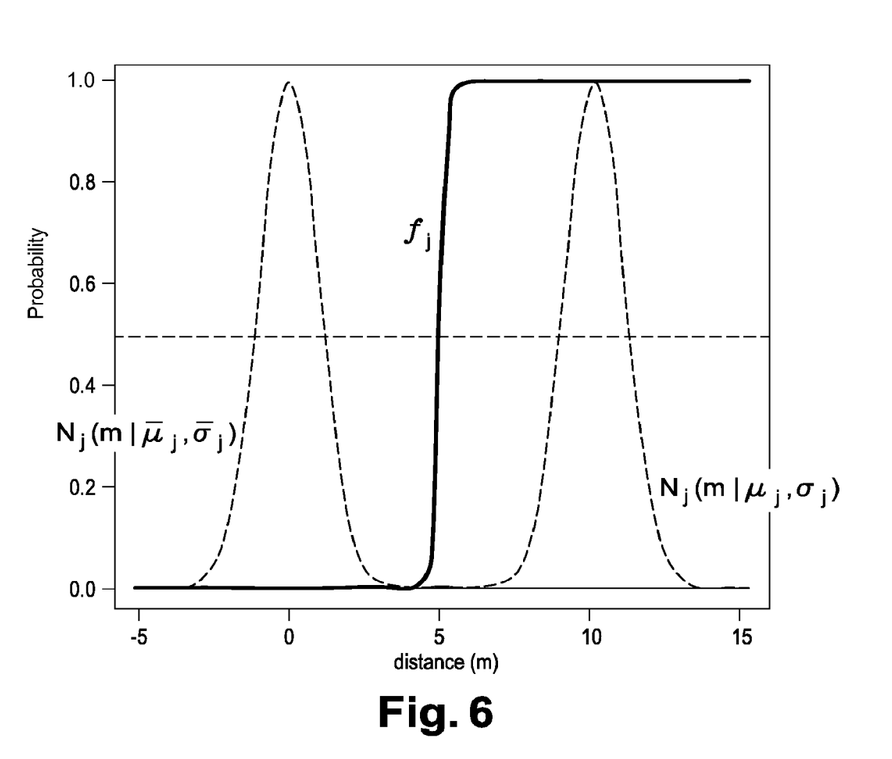
FIG. 6 is a diagram illustrating two Gaussian distributions and a probability function obtained therefrom.

The method carries on with the calculation, at step 20, of a probability function $f_j$ for each microorganism j which separates distributions $N_j(m|\mu_j,\sigma_j)$ and $N_j(m|\overline{\mu}_j,\overline{\sigma}_j)$, as illustrated in FIG. 6.

More particularly, function $f_j$ fulfills relation:

$$f_j(m) = \frac{p_j \times N_j(m|\mu_j,\sigma_j)}{p_j \times N_j(m|\mu_j,\sigma_j) + (1-p_j) \times N_j(m|\overline{\mu}_j,\overline{\sigma}_j)} \quad (7)$$

where $p_j$ is a predetermined setting parameter relative to a priori information regarding the prevalence of microorganism j.

Parameter $p_j$ is for example equal to 0.5 if event "distance m corresponds to microorganism j" has the same weight as event "distance m corresponds to a microorganism different from microorganism j". Under this assumption, it is considered that if m is equidistant from the 2 distributions, the spectrum has a probability of $$\frac{1}{2}$$

of being reference microorganism j, and accordingly a probability of $$\frac{1}{2(N-1)}$$

of being any of the N−1 other reference microorganisms, where N is the number of microorganisms recorded in the knowledge base.

As a variation, parameter $p_j$ is equal to $$\frac{1}{N},$$

where N is the number of microorganisms recorded in the knowledge base. Under this assumption, it is considered that if m is equidistant from the 2 distributions, the spectrum has the same probability of being any of the reference microorganisms.

As illustrated in FIG. 6, probability function $f_j$ is a function which is monotonous at least over a distance interval comprising most of distributions $N_j(m|\mu_j,\sigma_j)$ and $N_j(m|\bar{\mu}_j,\bar{\sigma}_j)$, and which increases from 0 to 1 by taking the form of a sigmoid. Particularly, for high values of $N_j(m|\bar{\mu}_j,\bar{\sigma}_j)$, this function is equal to 0 while for high values of $N_j(m|\mu_j,\sigma_j)$, this function is equal to 1.

Function $f_j$ indeed represents a degree of likelihood for a microorganism having a distance m to boundary $F_j$ to be microorganism j. More particularly, it is shown that function $f_j$ corresponds to probability $p(s|m)$ for a tested microorganism to be microorganism j when distance m is observed, that is, function $f_j$ according to relation 7 corresponds to probability $p(s|m)$ according to relations:

$$p(s \mid m) = \frac{p(s)p(m \mid s)}{p(m)} \tag{8}$$

$$p(m) = p(s)p(m \mid s) + p(\bar{s})p(m \mid \bar{s}) \tag{9}$$

where $p(s)$ is an a priori distribution of the probability of obtaining microorganism j, that is, its prevalence, $p(m|s)$ is the likelihood of distance m for microorganism j, and $p(m|\bar{s})$ is the likelihood of distance m for the other microorganisms. Thus, according to the invention, $p(s)=p_j$, $p(m|s)=N_j(m|\mu_j,\sigma_j)$, and $p(m|\bar{s})=N_j(m|\bar{\mu}_j,\bar{\sigma}_j)$.

Figure 7:
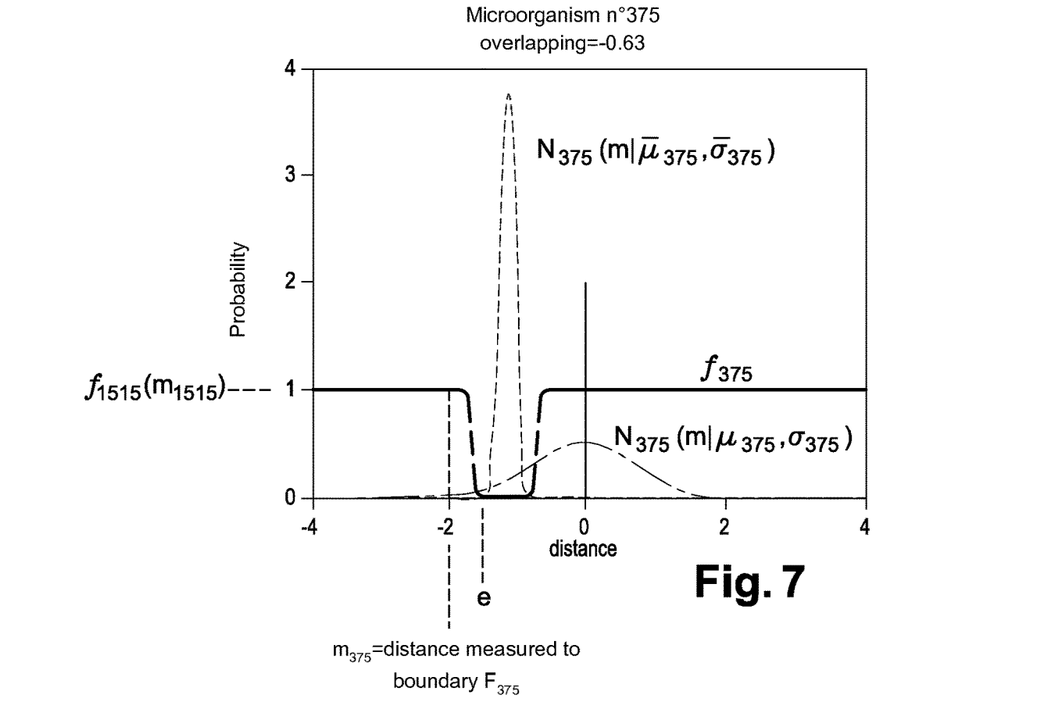
FIGS. 7 and 8 are diagrams illustrating the lack of monotony capable of appearing in probability functions according to the invention.
Figure 8:
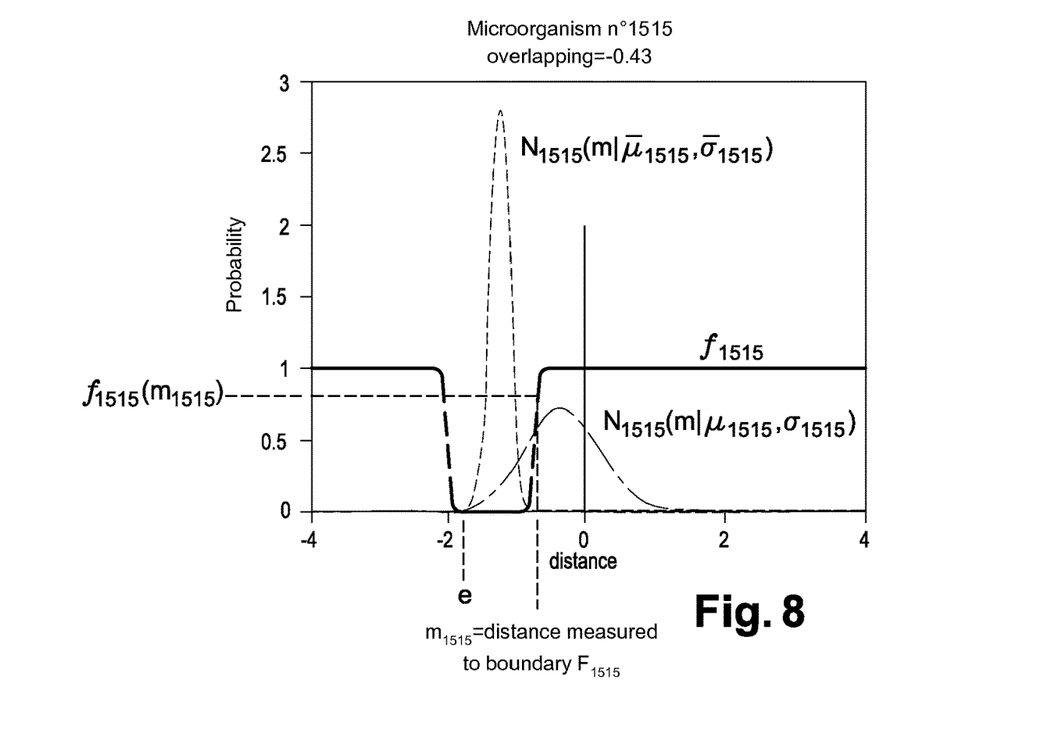

Although the case of the distributions discussed in FIG. 6 is standard, function $f_j$ may sometimes not be monotonous on an end portion of a distribution, as shown in FIGS. 7 and 8.

Indeed, the selected distribution model $N_j(m|\mu_j,\sigma_j)$ and $N_j(m|\bar{\mu}_j,\bar{\sigma}_j)$ may be inaccurate, or the number of samples used to generate calibration values $\{V_{i,j}^c\}$ and $\{V_{i,k\neq j}^c\}$ may be limited, and thus induce an uncertainty on the distribution parameters or, also, aberrant distance values may be generated, for example, due to measurement uncertainties.

Particularly, the function of transformation into probabilities $f_j$ calculated from normal laws such as defined in relations (1) to (6) may not be monotonous. In particular, the two normal distributions $N_j(m|\mu_j,\sigma_j)$ and $N_j(m|\bar{\mu}_j,\bar{\sigma}_j)$ have standard deviations $\sigma_j$ and $\bar{\sigma}_j$ which are most often very different, distribution $N_j(m|\bar{\mu}_j,\bar{\sigma}_j)$ associated with the non-representatives of microorganism j being generally much narrower than distribution $N_j(m|\mu_j,\sigma_j)$ of the representatives of microorganism j. This often translates as a non-monotonous character of function $f_j$ over all distances, particularly as a rise of function $f_j$ for distances "to the left" of distribution $N_j(m|\bar{\mu}_j,\bar{\sigma}_j)$, as illustrated in FIGS. 7 and 8.

For example in FIG. 7, for a distance $m_{375}$ between a microorganism to be identified and boundary $F_{375}$ associated with microorganism No. 375 of the knowledge base equal to −2, with no specific measurement, function $f_{375}$ of microorganism No. 375 is equal to 1. This means that the microorganism to be identified is microorganism No. 375 with a probability close to 100%, although, on the contrary, the real probability for the measured microorganism to be microorganism No. 375 appears to be very low. Further, there exist other functions $f_j$ for which the value will be positive for distance m of the microorganism to be identified to boundary $F_j$ associated with microorganism j, and thus an associated probability much greater than 0. For example, in FIG. 8, probability $f_{375}(m_{375})$ of the microorganism to be identified, associated with distance $m_{375}$ thereof to boundary $F_{1515}$ of a microorganism No. 1515 of the knowledge base, is equal to 0.9, that is, a probability lower than that associated with microorganism No. 375, while the microorganism to be identified effectively appears to be microorganism No. 1515. The reliance on this identification to microorganism No. 1515 should thus be greater than that associated with microorganism No. 375.

Although, in reality, it is unlikely to obtain distances measured in end portions of functions $f_j$ where such a behavior might exist, function $f_j$ is advantageously determined to keep its monotonous character.

It should be noted on this regard that Gaussian distributions are advantageously selected due to the simplicity of their calculation, and that the non-monotonous behavior which may in certain cases result from this choice is not critical. Indeed, the use of Gaussian curves has the advantage of generating functions $f_j$ having an analytically-predictable behavior. It is thus possible to modify functions $f_j$ according to relation (7) to guarantee in the end a monotonous behavior over all distances.

More particularly, it is shown that for a function $f_j$ based on Gaussian distributions, there can only exist a single local minimum having a value according to the following relation:

$$e = \frac{\bar{\mu}_j \sigma_j^2 - \mu_j \bar{\sigma}_j^2}{\sigma_j^2 - \bar{\sigma}_j^2} \tag{10}$$

Advantageously, the method thus carries on with a step 22 where functions $f_j$ are made monotonous. More specifically, the following is set down:

$f_j(m)=0$ for any $m \leq e$, if $\mu > \bar{\mu}$, or equivalently $\sigma > \bar{\sigma}$ (11)

$f_j(m)=1$ for any $m \geq e$, if logic relation "$\mu > \bar{\mu}$"$\oplus$"$\sigma > \bar{\sigma}$" is true (12)

where $\oplus$ is the symbol of the "exclusive-or" logic function.

Figure 9:
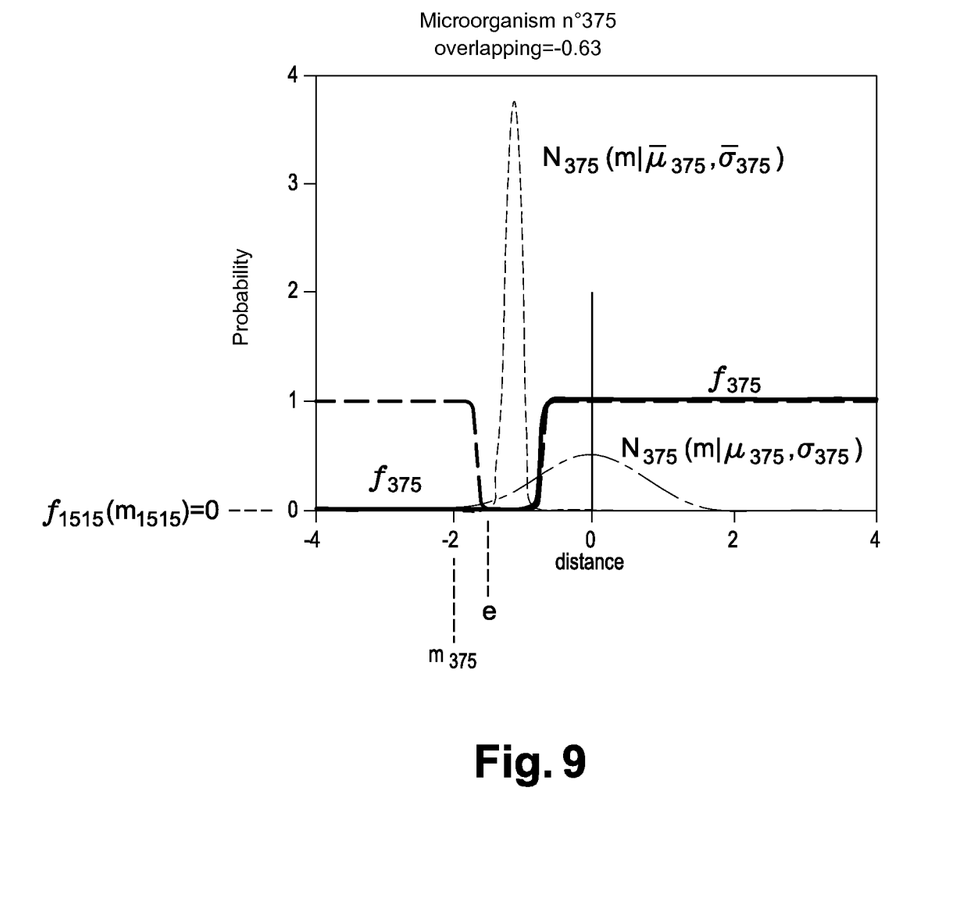
FIG. 9 is a diagram illustrating the result of the forcing of a probability function according to the invention to be monotonous.

An application of step 22 is for example illustrated in FIG. 9 where function $f_{375}$ illustrated in FIG. 7 is forced to the zero value for any distance shorter than value e, so that function $f_{375}$ now is a sigmoid monotonous function over all distances.

At the end of step 22, the classification tool according to the invention is thus calibrated. Boundaries $F_j$ of the OVA SVM classification tool as well as probability functions $f_j$ are stored in the knowledge base.

The knowledge base is incorporated in a system of microorganism identification by mass spectrometry comprising a mass spectrometer, for example, a MALDI-TOF mass spectrometer, as well as a data processing unit, connected to the spectrometer and capable of receiving and processing the acquired mass spectrums to identify unknown microorganisms.

More particularly, for the identification of an unknown microorganism, the method comprises a step 24 of acquiring one or a plurality of mass spectrums thereof, a step 26 of preprocessing the acquired spectrums, as well as a step 28 of detecting peaks of the spectrums and of determining a peak vector $V_m$, such as for example previously described in relation with steps 10 to 14.

At a next step 30, distance $m_j$ of vector $V_m$ to each of boundaries $F_j$ is calculated, after which each of distances $m_j$ is transformed, at step 32, into the corresponding probability $f_j(m_j)$.

In a first variation, probabilities $f_j(m_j)$ are numerically calculated according to formulas (1), (2), and (7), that is, according to a relation of the following type:

$$f_j(m) = \frac{p_j \times \frac{1}{\sigma_j \sqrt{2\pi}} \cdot \exp\left(-\frac{1}{2}\left(\frac{m-\mu_j}{\sigma_j}\right)^2\right)}{p_j \times \frac{1}{\sigma_j \sqrt{2\pi}} \cdot \exp\left(-\frac{1}{2}\left(\frac{m-\mu_j}{\sigma_j}\right)^2\right) + (1-p_j) \times \frac{1}{\overline{\sigma}_j \sqrt{2\pi}} \cdot \exp\left(-\frac{1}{2}\left(\frac{m-\overline{\mu}_j}{\overline{\sigma}_j}\right)^2\right)} \quad (13)$$

In this variation, the numerator and the denominator are calculated independently from each other by implementing numerical exponential functions. However, when a microorganism has a distance $m_j$ far from averages $\mu_j$ and $\overline{\mu}_j$ of the two Gaussian distributions, the resulting numerical exponential functions risk being approximated to 0, which would result in an indetermination of 0/0 type for value $f_j(m_j)$.

According to a second variation, probabilities $f_j(m_j)$ are calculated according to relation (14) hereafter:

$$f_j(m) = \frac{1}{1 + \frac{1-p_j}{p_j} \exp\left(\ln\left(\frac{\sigma_j}{\overline{\sigma}_j}\right) - \frac{1}{2(\sigma_j \overline{\sigma}_j)^2}\left[\frac{(\sigma_j - \overline{\sigma}_j)m_j - }{(\overline{\mu}_j \sigma_j - \mu_j \overline{\sigma}_j)}\right]\left[\frac{(\sigma_j + \overline{\sigma}_j)m_j - }{(\overline{\mu}_j \sigma_j + \mu_j \overline{\sigma}_j)}\right]\right)}$$

Relation (13) is strictly equivalent to relation (14) from a mathematical viewpoint. However, relation (14) is more robust to numerical approximations and even stands distances of infinite value without causing any indetermination.

In the case where functions $f_j$ are forced to be monotonous, relations (11) and (12) are also applied.

Probabilities $f_j(m_j)$ are then classified by decreasing order. If none exceeds a given threshold, it is for example considered that there is no identification. If, on the contrary, one or several exceed a given threshold, they are for example displayed, at step 34, on a display of the identification system, with a list of associated microorganisms. For example, a list of 3 microorganisms is displayed with their corresponding value of $f_j(m_j)$ which directly corresponds to the degree of reliance which can be had on the microorganism identification.

Figure 10:
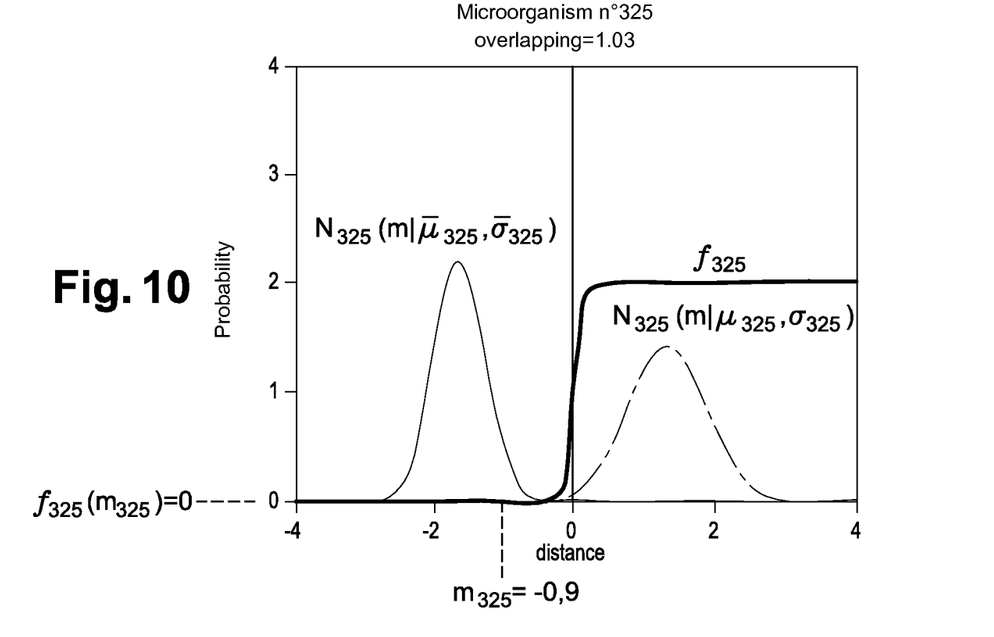
FIGS. 10 and 11 are drawings illustrating a case of difficult identification by means of the classification tool, solved by the invention.
Figure 11:
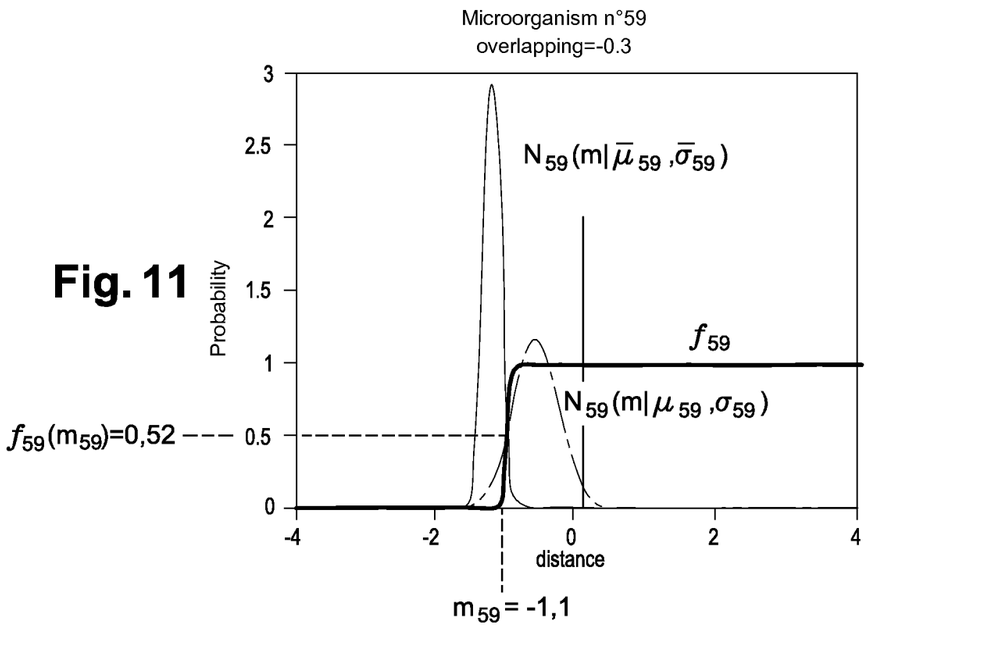

FIGS. 10 and 11 illustrate a case of particularly difficult identification of a microorganism by the classification tool, solved by the invention. FIG. 10 is a diagram illustrating Gaussian distributions $N_{325}(m|\mu_{325},\sigma_{325})$ and $N_{325}(m|\overline{\mu}_{325},\overline{\sigma}_{325})$, as well as their associated functions $f_{325}$, corresponding to an organism No. 325 of the knowledge base, and FIG. 11 is a diagram illustrating Gaussian distributions $N_{59}(m|\mu_{59},\sigma_{59})$ and $N_{59}(m|\overline{\mu}_{59},\overline{\sigma}_{59})$, as well as their functions $f_{59}$, corresponding to an organism No. 59 of the knowledge base. A distance $m_{59}$ of a microorganism to be identified to boundary $F_{59}$ of microorganism No. 59 is equal to −1.1, while distance $m_{325}$ of the microorganism to be identified to boundary $F_{325}$ of microorganism No. 325 is equal to −0.9.

According to the state of the art, which is based on the direct comparison of distances, with no additional analysis, it is thus concluded that the microorganism to be identified is microorganism No. 325. Now, if a closer look is taken at distributions, it can be seen that the microorganism to be identified has practically no chance of being microorganism No. 325, while it has good chances of being microorganism No. 59. Only an additional analysis, based on the know-how of the person in charge of the identification, is capable of concluding from the measured distances that the identified microorganism actually is No. 59.

The distance transformation according to probabilities according to the invention enables to solve this type of complex case. Indeed, function $f_{325}(m_{325})$ is zero, meaning that the probability for the microorganism to be identified to be microorganism No. 325 is zero, while function $f_{59}(m_{59})$ is positive, here, equal to 0.52, which means that the microorganism to be identified is microorganism No. 59 with a 52% reliance.

Advantageously, the method according to the invention also enables to judge whether or not the unknown microorganism is one of the reference microorganisms of the knowledge base. Indeed, values $f_j(m)$ represent measurements of the similarity of this microorganism with the reference microorganisms. Thus, if values $f_j(m)$ are low, it can be judged that the unknown microorganism is similar to none of the reference microorganisms, and is thus not referenced in the knowledge base.

More particularly, the method according to the invention comprises a step of comparing each of values $f_j(m)$ with a predetermined threshold value $s_j$, for example, unique for all reference microorganisms or a specific value for each of them, and if values $f_j(m)$ are all lower than their respective threshold values, it is then determined that the reference microorganism corresponds to none of the reference microorganisms in the knowledge base.

Advantageously, a single threshold value $s_j$ is used, this value being equal to 60%. The inventors have indeed observed that this value enables to determine reliably that an unknown microorganism is not contained in the knowledge base.

Advantageously, the method also returns close values $f_j(m)$, for example, maximum values $f_j(m)$ which differ from one another by less than 10%.

Although the method according to the invention enables to solve a significant number of difficult cases raising issues for the classifier based on which probability functions $f_j$ are determined, there however is a number of cases where the method according to the invention returns similar results for different reference organisms, particularly when reference microorganisms are very similar, for example, in terms of phenotype. Values $f_j(m)$ being measurements of similarity between microorganisms, the method according to the invention thus enables to return results having a substantially close value for intrinsically similar reference microorganisms that the classifier has failed to distinguish with a minimum margin.

A specific embodiment of the invention where Gaussian distributions are used to model random variables $N_j(m|\mu_j,\sigma_j)$ and $N_j(m|\bar{\mu}_j,\bar{\sigma}_j)$ has been described.

Other types of random variables are of course possible, provided to obtain a relevant distribution modeling. It is for example possible to select mixtures of Gaussian functions, to take into account the possible presence of several modalities in the distributions. Gaussian functions are advantageous since their identification is very simple and it has been observed that such a modeling, though imperfect, enables to obtain robust probability functions $f_j$.

Similarly, an embodiment where the classification tool used is a one-versus-all SVM algorithm has been described.

Of course, the invention is not limited to this type of algorithm and applies to any type of classification algorithm, particularly to multi-class classification algorithms obtained by combination of binary classifications of "one-versus-all" or "all-versus-all" type, for example, as soon as the classification algorithm generates a value or score representing a distance to reference objects which is not directly a reliance index.

As known per se, whatever the considered classification algorithm, there always exist scores or distance calculated with respect to data representing each of the reference microorganisms on which the method according to the invention can be based.

Particularly, the invention relates to classification algorithms applying a calculation of the similarity with reference elements, such as for example average spectrums, or "super spectrums" such as described in document EP 1 253 622.

In the algorithm described in document EP 1 253 622 B1, "synthetic background spectrums" (REFs), also called "super spectrums" are constructed and each corresponds to a list of peaks considered as the most typical of a given species. To identify a microorganism by means of a mass spectrum, a "similarity" of this measured spectrum with all the super spectrums stored in a knowledge base is calculated. This similarity may for example be a distance integrating a tolerance for masses, such as for example a Jaccard or Hamming distance.

Particularly, if SSp1 is a super spectrum formed of a list of masses M, and of associated weights $W_i$, and $Sp_1$ is a list of masses $M'_j$ associated with peaks detected in the mass spectrum of the microorganism to be identified, then the similarity, or tolerant distance, between SSp1 and Sp1 is calculated, as known per se, according to relation:

$$s(SSp1/Sp1) = \frac{\sum W_i, \exists M'_j, \frac{|M'_j - M_i|}{M} < d}{\sum W_i} \quad (15)$$

where d is the relative tolerance accepted between two masses.

Figure 12:
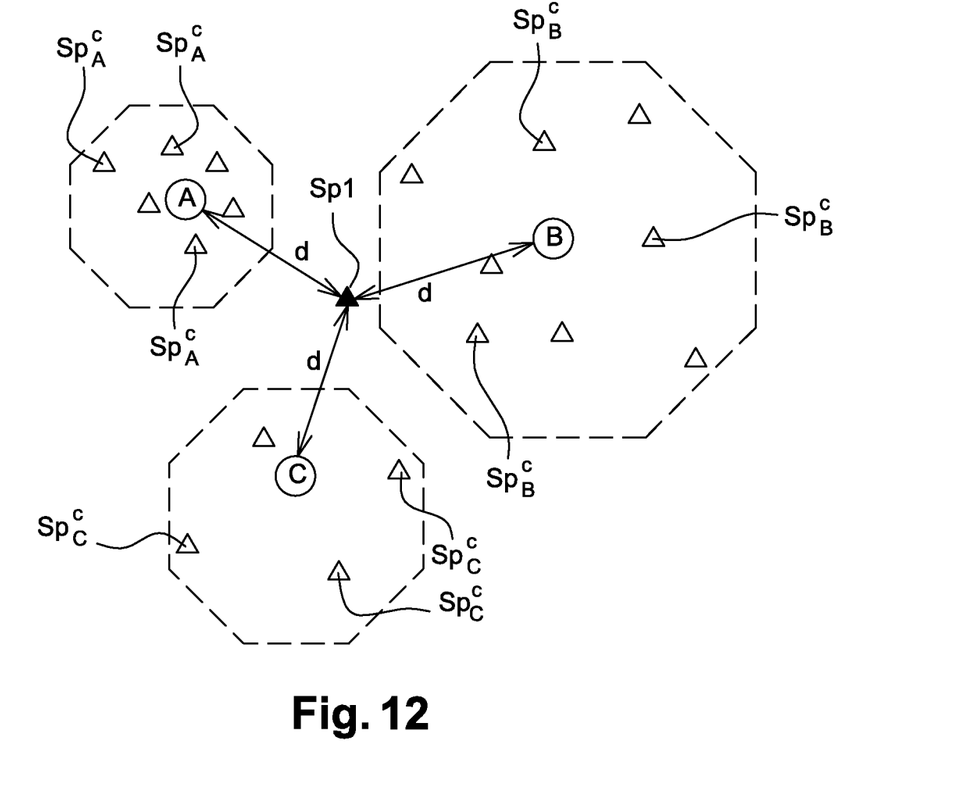
FIG. 12 is a diagram illustrating tolerant distances from a spectrum to be identified to super-spectrums according to the state of the art.

According to the state of the art, the organism corresponding to the super spectrum having the strongest similarity is retained as the identification, this similarity value being directly used as a measurement of the reliance that may be had on the result. Now, according to the selection of the peaks which have been used to build the super spectrum, the average similarities for all the spectrums of a species with their super-spectrum (REFs) are not necessarily the same. Thus, in the example illustrated in FIG. 12, although spectrum Sp1 is equidistant from the 3 super spectrums A, B, C, it should be understood that the probability for it to effectively be of species A is lower than that of being of species B, as clearly appears from the distribution of sample spectrums $\{Sp_A^c\}$, $\{Sp_B^c\}$, $\{Sp_C^c\}$ having been used as a basis for the construction of the super spectrums. The invention enables to normalize the obtained similarities and thus to raise this ambiguity.

What is claimed is:

1. A method of identifying by mass spectrometry a microorganism from among a predetermined set of reference microorganisms, each reference microorganism being represented by a set of reference data from mass spectrometry measurements of each said reference microorganism, the method being implemented in a data processing system comprising a mass spectrometer and a data processing unit connected to the mass spectrometer and to a knowledge base data storage unit, wherein the method comprises:
   determining, using the data processing unit, a set of data representative of the microorganism to be identified from a mass spectrometry measurement of said microorganism acquired from the mass spectrometer connected to said data processing unit; then
   for each reference microorganism, calculating, using the data processing unit, the set of reference data of each reference microorganism stored in the knowledge base data storage unit, and classification tools also stored in the knowledge base data storage unit, a distance m between said determined set of data representative of the microorganism to be identified and the set of reference data of the reference microorganism, said distance m being representative of the microorganism to be identified; then
   for each reference microorganism, calculating, using the data processing unit, a probability for the microorganism to be identified to be the reference microorganism, according to relation:

$$f(m) = \frac{pN(m|\mu, \sigma)}{pN(m|\mu, \sigma) + (1-p) \times N(m|\bar{\mu}, \bar{\sigma})}$$

where:
   m is the distance calculated between the determined set of data for the microorganism to be identified to the set of reference data of the reference microorganism;
   $f(m)$ is the probability calculated for said distance m;
   $N(m|\mu, \sigma)$ is a value, for the distance m, of a first random variable modeling the distance between the set of data associated with the microorganism to be identified and the set of reference data of the reference microorganism, when the microorganism to be identified is the reference microorganism;
   $N(m|\bar{\mu}, \bar{\sigma})$ is a value, for the distance m, of a second random variable modeling the distance between the set of data associated with the microorganism to be identified and the set of reference data of the reference microorganism, when the microorganism to be identified is not the reference microorganism;
   wherein the random variables $N(m|\mu, \sigma)$ and $N(m|\bar{\mu}, \bar{\sigma})$ are Gaussian random variables, having averages respectively equal to $\mu$ and $\bar{\mu}$, and standard deviations respectively equal to $\sigma$ and $\bar{\sigma}$; and
   p is a predetermined scalar in the range from 0 to 1, wherein the calculated probabilities for the microorganism to be each of the reference microorganisms are stored in the knowledge base data storage unit; then comparing, using the data processing unit, the calculated probabilities for the microorganism to be each of the reference microorganisms, and providing an identification decision for the microorganism based on the comparing of the calculated probabilities.

2. The identification method of claim 1, wherein, in the calculation of the probability $f(m)$, the relation $$f(m) = \frac{pN(m|\mu,\sigma)}{pN(m|\mu,\sigma)+(1-p)N(m|\bar{\mu},\bar{\sigma})}$$

is used in the form of relation:

$$f(m) = \frac{1}{1 + \frac{1-p}{p}\exp\left(\ln\left(\frac{\sigma}{\bar{\sigma}}\right) - \frac{1}{2(\sigma\bar{\sigma})^2}\left[\frac{(\sigma-\bar{\sigma})m - }{(\bar{\mu}\sigma - \mu\bar{\sigma})}\right]\left[\frac{(\sigma+\bar{\sigma})m - }{(\bar{\mu}\sigma + \mu\bar{\sigma})}\right]\right)}$$

3. The identification method of claim 1, wherein if logic relation "$\mu > \bar{\mu}$"$\oplus$"$\sigma > \bar{\sigma}$" is verified, where $\oplus$ represents the "exclusive-or" function, the probability $f(m)$ is set to 1 for any distance m greater than $$\frac{\bar{\mu}\sigma^2 - \mu\bar{\sigma}^2}{\sigma^2 - \bar{\sigma}^2}.$$

4. The identification method of claim 1, wherein if logic relation "$\mu,\bar{\mu}$"$\oplus$"$\sigma > \bar{\sigma}$" is not verified, where $\oplus$ represents the "exclusive-or", the probability $f(m)$ is set to 0 for any distance m smaller than $$\frac{\bar{\mu}\sigma^2 - \mu\bar{\sigma}^2}{\sigma^2 - \bar{\sigma}^2}.$$

5. The identification method of claim 1, wherein the predetermined scalar p is identical for all reference microorganisms.

6. The identification method of claim 5, wherein the predetermined scalar p is equal to $$\frac{1}{N},$$

where n is the size of the set of reference microorganisms.

7. The identification method of claim 5, wherein the predetermined scalar p is equal to 0.5.

8. The identification method of claim 1, wherein the calculation of the distance between the acquired spectrum and each reference microorganism is implemented by a vectorial classification algorithm.

9. The identification method of claim 8:
wherein the determination of the mass spectrum of the microorganism comprises:
acquiring at least one mass spectrum of said microorganism;
detecting peaks in the at least one acquired mass spectrum and converting the detected peaks into a vector of a predetermined vectorial space;
and wherein the calculation of the distance between said microorganism and each reference microorganism comprises calculating an algebraic distance between the determined vector and a boundary which partitions the vectorial space between a first sub-space characteristic of the reference microorganism and a second sub-space characteristic of the other reference microorganisms.

10. The identification method of claim 9, wherein the boundary of a reference microorganism is calculated by means of an algorithm of "support vector machine" type and of a set of vectors corresponding to the reference microorganisms.

11. The identification method of claim 8, wherein a vector of the vectorial classification algorithm is calculated by identifying at most one peak in each interval of a predetermined subdivision in a range of mass-to-charge ratios of the mass spectrum.

12. The identification method of claim 1, wherein the calculation of the distance between the acquired spectrum and each reference microorganism is implemented by a tolerant distance algorithm.

13. The identification method of claim 1, wherein the method comprises:
comparing each of the probabilities $f(m)$ with a predetermined threshold value; and
determining that the microorganism to be identified corresponds to none of the reference microorganisms if all the probabilities $f(m)$ are smaller than the predetermined threshold value.

14. The identification method of claim 13, wherein the predetermined threshold value is equal to 60%.

15. The method of claim 1, further comprising displaying an identification decision of the microorganism on a display associated with the data processing system.

16. A device for identifying a microorganism by mass spectrometry, comprising:
a mass spectrometer adapted to generate mass spectrums of microorganisms to be identified;
a data processing unit connected to the mass spectrometer and to a knowledge base data storage unit, and adapted to identify the microorganism associated with the mass spectrums generated by the spectrometer by implementing the following actions:
determining, by the data processing unit, a set of data representative of the microorganism to be identified from a mass spectrometry measurement of said microorganism acquired from said mass spectrometer connected to said data processing unit; then
for each reference microorganism, being represented by a set of reference data from mass spectrometry measurements of each said reference microorganism, calculating, by the data processing unit using classification tools, a distance m between said determined set of data representative of the microorganism to be identified and the set of reference data of the reference microorganism, said distance m being representative of the microorganism to be identified, the set of reference data of each reference microorganism being stored in the knowledge base data storage unit, and the classification tools also being stored in the knowledge base data storage unit, for each reference microorganism, calculating, by the data processing unit, a probability for the microorganism to be identified to be the reference microorganism, according to relation:

$$f(m) = \frac{pN(m|\mu, \sigma)}{pN(m|\mu, \sigma) + (1-p)N(m|\overline{\mu}, \overline{\sigma})}$$

where:
- m is the distance calculated between the determined set of data for the microorganism to be identified to the set of reference data of the reference microorganism;
- $f(m)$ is the probability calculated for said distance m;
- $N(m|\mu, \sigma)$ is a value, for the distance m, of a first random variable modeling the distance between the set of data associated with the microorganism to be identified and the set of reference data of the reference microorganism, when the microorganism to be identified is the reference microorganism;
- $N(m|\overline{\mu}, \overline{\sigma})$ is a value, for the distance m, of a second random variable modeling the distance between the set of data associated with the microorganism to be identified and the set of reference data of the reference microorganism, when the microorganism to be identified is not the reference microorganism;
- wherein the random variables $N(m|\mu, \sigma)$ and $N(m|\overline{\mu}, \overline{\sigma})$ are Gaussian random variables, having averages respectively equal to $\mu$ and $\overline{\mu}$, and standard deviations respectively equal to $\sigma$ and $\overline{\sigma}$; and
- p is a predetermined scalar in the range from 0 to 1,
- wherein the calculated probabilities for the microorganism to be each reference microorganism are stored in the knowledge base data storage unit,
- comparing, by the data processing unit, the calculated probabilities for the microorganism to be identified to be each of the reference microorganisms, and
- providing an identification decision for the microorganism based on the comparing of the calculated probabilities.

17. The device of claim 16, wherein, in the calculation of the probability $f(m)$, the relation $$f(m) = \frac{pN(m|\mu, \sigma)}{pN(m|\mu, \sigma) + (1-p)N(m|\overline{\mu}, \overline{\sigma})}$$

is used in the form of relation:

$$f(m) = \frac{1}{1 + \frac{1-p}{p}\exp\left(\ln\left(\frac{\sigma}{\overline{\sigma}}\right) - \frac{1}{2(\sigma\overline{\sigma})^2}[(\sigma - \overline{\sigma})m - (\overline{\mu}\sigma - \mu\overline{\sigma})]\right.}$$
$$\left.[(\sigma + \overline{\sigma})m - (\overline{\mu}\sigma + \mu\overline{\sigma})]\right)}.$$

18. The device of claim 16, wherein if logic relation "$\mu > \overline{\mu}$"$\oplus$"$\sigma > \overline{\sigma}$" is verified, where $\oplus$ represents the "exclusive-or" function, the probability $f(m)$ is set to 1 for any distance m greater than $$\frac{\overline{\mu}\sigma^2 - \mu\overline{\sigma}^2}{\sigma^2 - \overline{\sigma}^2}.$$

19. The device of claim 16, wherein if logic relation "$\mu > \overline{\mu}$"$\oplus$"$\sigma > \overline{\sigma}$" is not verified, where $\oplus$ represents the "exclusive-or", the probability $f(m)$ is set to 0 for any distance m smaller than $$\frac{\overline{\mu}\sigma^2 - \mu\overline{\sigma}^2}{\sigma^2 - \overline{\sigma}^2}.$$

20. The device of claim 16, further comprising a display, wherein an identification decision of the microorganism is displayed on the display.

\* \* \* \* \*